United States Patent [19]

Tenta

[11] 4,112,121

[45] * Sep. 5, 1978

[54] METHOD AND COMPOSITION FOR THE TREATMENT OF SEBORRHEIC KERATOSIS

[76] Inventor: Louis T. Tenta, 6007 N. Sheridan Rd., Chicago, Ill. 60660

[*] Notice: The portion of the term of this patent subsequent to Jun. 28, 1994, has been disclaimed.

[21] Appl. No.: 821,392

[22] Filed: Aug. 3, 1977

Related U.S. Application Data

[63] Continuation of Ser. No. 704,448, Jul. 12, 1976, abandoned.

[51] Int. Cl.$^2$ ............................................ A61K 31/05
[52] U.S. Cl. .............................. 424/346; 424/DIG. 13
[58] Field of Search ................ 424/343, DIG. 13, 346

[56] References Cited

U.S. PATENT DOCUMENTS 3,821,370  6/1974  Tenta ................................. 424/343

OTHER PUBLICATIONS

Remington's Pharm. Sciences, 13th Ed. (1965), p. 535.
Merck Index, 7th Ed. (1960), pp. 429, 863.

*Primary Examiner*—V. D. Turner
*Attorney, Agent, or Firm*—Hill, Gross, Simpson, Van Santen, Steadman, Chiara & Simpson

[57] ABSTRACT

Method and composition for the chemexfoliation (chemical exfoliation) of seborrheic keratosis and related conditions, the composition consisting essentially of an alkali metal or ammonium phenate, a monohydric alcohol, a polyhydric alcohol humectant and a gelling agent.

10 Claims, No Drawings

METHOD AND COMPOSITION FOR THE TREATMENT OF SEBORRHEIC KERATOSIS

This is a continuation, of application Ser. No. 704,448, filed July 12, 1976 now abandoned.

BACKGROUND OF THE INVENTION

1. Field of the Invention

This invention is in the field of topical compositions for the treatment of seborrheic keratosis and includes an alkali metal or ammonium phenate, a monohydric alcohol solvent, a polyhydric alcohol humectant which absorbs moisture from the air to initiate the exfoliation reaction, and a gelling agent which improves the adherence of the composition to the skin.

2. Description of the Prior Art

In U.S. Pat. No. 3,821,370, I described a topical composition for use in the treatment of various skin conditions, including seborrheic keratosis. This patent disclosed a composition containing from 20 to 60 parts of an inhibited phenol calculated as potassium phenolate, 1 part of a salicylate calculated as sodium salicylate, 5 parts of resorcinol, and 4 parts of a zinc compound calculated as zinc sulfate.

In a later filed application, now U.S. Pat. No. 3,949,072, I described a composition containing an inhibited phenol, a salicylate, a zinc compound and resorcinol, all dissolved in a nonaqueous solvent which included a hydrophilic non-toxic lower aliphatic alcohol. The advantage of the composition described in this later patent was the use of significantly lower amounts of the phenolate than in the previous patent.

SUMMARY OF THE INVENTION

The present invention relates to an improved topical composition for application to the skin to improve the external appearance of a skin blemished by the presence of certain skin disorders.

The skin is composed of two layers, a thin outer layer, the epidermis, which is about 0.1 mm. in thickness and a deeper, thicker layer, the dermis, of up to 2 to 4 mm. in thickness, depending upon its location in the human body.

The epidermis is composed of cells arranged in layers, with the outermost layer cells thickened or, as it is sometimes known, keratinized or hornified. Pigment cells are present in the deepest layer as well as in the "parent" cells which give rise to generations of younger cells to replace those lost to attrition and to wear and tear.

The dermis contains blood vessels and nerves which provide nutrition and sensation, respectively. Moreover, there are lymphatic vessels present which might be thought of as conveying "tissue juices". Additionally, the structures from which hairs grow (follicles) and glands which lubricate the skin are contained in the dermis. From these structures project small tubes or channels which penetrate the epidermis and open upon the surface of the skin in the form of hairs and/or pores. These structures of the dermis (vessels, nerves, follicles and glands) are surrounded by cells which are referred to as connective tissue cells. These cells may be considered as a support or superstructure for the overlying epidermis as well as supporting the vessels, nerves, follicles and glands within the dermis proper.

Moreover, intertwined among these various cells and structures contained within the dermis are elastic threads or fibers which permit the skin to regain shape after stretching. Additionally, the connective tissue cells are involved in the repair of these tissues from injurious or noxious sources. The repaired area of the tissue is manifested as a scar.

Many disorders may affect the skin. Some are a consequence of a local effect (such as a laceration, or cut) while others may reflect underlying constitutional disorders (such as the yellowing of skin that may occur in liver diseases).

Of those disorders that might be considered as arising from disturbances that are local in nature, certain ones will now be selectively discussed. Various changes occur which may affect the structure of anatomy of the skin. These changes may be manifested as a thickening of the outermost (keratinized or hornified) layer of the epidermis, and the resulting formation of brown or beige-colored warty-like areas (seborrheic keratosis). A change in the pigmentation of the skin may occur which produces random areas of brownish or tan discoloration. Moreover, unsightly scarring may occur as a consequence of acne eruptions or from superficial burns. A loss of the elastic fibers necessary for normal skin consistency may result from the stretch marks of obesity or pregnancy or from the effects of wasting scars.

Additionally, certain types of "birth marks" (which usually result from abnormally formed and expanded blood vessels) affect the color of the skin. Aging alters the skin structure by causing a weakness of the elastic fibers which results in a relaxation of the skin and consequent wrinkling. The objectionable external appearance caused by these disorders may be minimized or corrected in a nonsurgical fashion by the application of a composition, such as that disclosed herein, which is not harmful to one's health and which produces two fundamental and simultaneous reactions, one in the epidermis and another in the dermis.

These reactions occur at the site of the basic disorder and produce two responses, the one response being that of a superficial slough of the epidermis, and the other response being a stimulation of the connective tissue cells in the dermis. These responses, in turn, are manifest by a peeling of the outermost skin layer and the consequent removal of surface irregularities, blemishes and discolorations, and by a strengthening of the underlying dermis which results from an increase in the numbers of connective tissue cells which surround and support the hair follicles, glands and vessels. This produces a firmer and more consistent support for the skin, which is manifest by a minimizing of depressions, wrinkles and scars. Moreover, this same response may cause the obliteration or collapse of certain poorly formed blood vessels in the dermis and result in the disappearance or fading of certain types of birth marks.

The present invention provides a composition which does not require the salicylate, the resorcinol, nor the zinc compound provided in my previous compositions. Instead, my new chemexfoliation composition includes an alkali metal or ammonium phenate, a monohydric alcohol, either aliphatic or aromatic, a polyhydric alcohol humectant and a gelling agent. The function of the humectant is to absorb moisture from the air (or from the skin) to cause the phenate to decompose and free phenol. The gelling agent provides a means for adhering the composition in a stable manner to the skin surface.

DESCRIPTION OF THE PREFERRED EMBODIMENTS

The compositions of the present invention include an alkali metal or ammonium phenate in an amount sufficient to provide a concentration of 4 to 20 weight % of free phenol. In the case of potassium phenate which has a molecular weight of 133, 1 gram of the potassium phenate would liberate 0.7067 grams of phenol having a molecular weight of 94. The inhibited phenol of the present invention may thus be either potassium phenate, sodium phenate or ammonium phenate. These phenates can be produced by neutralizing 90% phenol with a corresponding alkali metal or ammonium hydroxide. The product is then recovered by crystallization with ether.

The reaction of the phenate with moisture from the air or from the skin is accelerated by the inclusion of a non-aqueous solvent consisting of a hydrophilic monohydric alcohol which may be aliphatic or aromatic. I prefer to use a lower aliphatic, non-toxic alcohol containing from 2 to 4 carbon atoms. The alcohol apparently absorbs significant amounts of moisture and initiates the reaction on the skin which is characterized by warmth and redness or blushing of the skin. This response is followed quickly in turn by a frosting of the skin and a sensation of tautness or tightening. These reactions occur within minutes after the application of the composition. Over the next 3 to 5 days, the skin takes on the character of an onion skin, somewhat rusty or violaceous in color, following which a flaking or peeling occurs which exposes from beneath a clear, cleaner, smoother appearing surface. The monohydric alcohol or combination of alcohols is added in an amount of from 25 to 85% by weight.

The composition also includes a polyhydric alcohol humectant in an amount of from 5 to 35 weight %. The particularly preferred humectants are ethylene glycol and propylene glycol. The hygroscopic nature of these glycols is well known. Ethylene glycol, for example, can absorb twice its weight of water at 100% relative humidity. The humectants, therefore, accelerate the reaction by absorbing significant quantities of moisture from the atmosphere to initiate the chemexfoliation.

The compositions of the present invention are employed in gel form. Any non-toxic gel-forming agent can be used for this purpose, but I particularly prefer to use cellulose derivatives such as hydroxyethylcellulose or carboxymethylcellulose. The gelling agent is added in an amount of about 5 to 15% by weight. The addition of such gelling agents enhances the reaction by providing a means for adhering the composition in a stable manner to the skin surface and permitting the hygroscopic action of the alcohol and the glycol to occur.

The following specific examples describe compositions which can be used according to the present invention.

EXAMPLE 1

A solution was made up containing 28.46% by weight potassium phenate, 35.77% by weight propylene glycol and 35.77% by weight ethanol. This solution contained 20.11% free phenol. 40.15 grams of this solution were combined with 2.63 grams of hydroxyethylcellulose to provide a gel which contained 6.15% hydroxyethylcellulose. The gel was stable and could be readily applied to the affected areas of the skin.

EXAMPLE 2

A solution was made up containing 21.20% potassium phenate, 39.29% propylene glycol, and 39.20% ethanol. This solution contained 14.98% free phenol. 40.02 grams of the solution were combined with 2.93 grams of hydroxyethylcellulose to produce a gel containing 6.82% by weight hydroxyethylcellulose.

EXAMPLE 3

A solution was made up containing 14.23% potassium phenate, 42.88% propylene glycol, and 42.88% ethanol. This solution contained 10.05% free phenol. 40.08 grams of the solution were combined with 4.3 grams of hydroxyethylcellulose to produce a stable gel containing 9.69% by weight hydroxyethylcellulose.

EXAMPLE 4

A solution was made up containing 7.11% potassium phenate, 46.44% propylene glycol, and 46.44% ethanol. This solution contained 5.02% free phenol. 40.22 grams of the solution were combined with 5.20 grams of hydroxyethylcellulose to produce a stable gel having a hydroxyethylcellulose concentration of 11.45% by weight.

The chemexfoliation agents of the present invention are easy to apply and adhere well to the surface of the skin. While the dosage level will depend, of course, upon the severity of the condition, I have found it is possible to employ a gel containing 1 gram of potassium phenate to treat approximately 200 square centimeters of skin.

It should be evident that modifications can be made to the described embodiments without departing from the scope of the present invention.

I claim as my invention:

1. A chemexfoliation composition for the treatment of seborrheic keratosis consisting essentially of an alkali metal or ammonium phenate in an amount sufficient to provide a concentration of 4 to 20 weight % calculated as free phenol, a monohydric alcohol in an amount of from 25 to 85 weight %, a polyhydric alcohol humectant in an amount of from 5 to 35 weight %, and a pharmacologically acceptable, non-toxic gelling agent in an amount of from 5 to 15 weight %, said gelling agent providing a means for adhering the composition to the skin surface.

2. The composition of claim 1 in which said phenate is potassium phenate.

3. The composition of claim 1 in which said monohydric alcohol is ethanol.

4. The composition of claim 1 in which said humectant is ethylene glycol.

5. The composition of claim 1 in which said humectant is propylene glycol.

6. The composition of claim 1 in which said gelling agent is hydroxyethylcellulose.

7. The composition of claim 1 in which said gelling agent is carboxymethylcellulose.

8. A chemexfoliation composition for the treatment of seborrheic keratosis consisting essentially of potassium phenate in an amount sufficient to provide a free phenol concentration of from 4 to 20 weight %, ethanol in an amount of from 25 to 85 weight %, ethylene glycol in an amount of from 5 to 35 weight %, and a pharmacologically acceptable, non-toxic hydroxyethylcellulose in an amount of from 5 to 15 weight % and sufficient to cause the formation of a stable gel, said hydroxyethylcellulose providing a means for adhering the composition to the skin surface.

9. A method for treating an affected skin area to minimize the objectionable appearance of seborrheic keratosis which comprises applying to the affected area the composition of claim 1.

10. A method for treating an affected skin area to minimize the objectionable appearance of seborrheic keratosis which comprises applying to the affected skin area the composition of claim 8.

* * * * *